(12) United States Patent
Yoon et al.

(10) Patent No.: US 10,130,243 B2
(45) Date of Patent: Nov. 20, 2018

(54) IMAGE-BASED FEEDBACK ENDOSCOPY SYSTEM

(71) Applicants: Woon Jong Yoon, Bothell, WA (US); Eric J. Seibel, Seattle, WA (US); Matthew R. Burkhardt, Pasadena, CA (US); Timothy D. Soper, Sunnyvale, CA (US)

(72) Inventors: Woon Jong Yoon, Bothell, WA (US); Eric J. Seibel, Seattle, WA (US); Matthew R. Burkhardt, Pasadena, CA (US); Timothy D. Soper, Sunnyvale, CA (US)

(73) Assignee: Qatar University Al Tarfa, Doha (QA)

( * ) Notice: Subject to any disclaimer, the term of this patent is extended or adjusted under 35 U.S.C. 154(b) by 722 days.

(21) Appl. No.: 14/611,114

(22) Filed: Jan. 30, 2015

(65) Prior Publication Data

US 2015/0208904 A1    Jul. 30, 2015

Related U.S. Application Data

(60) Provisional application No. 61/933,758, filed on Jan. 30, 2014.

(51) Int. Cl.
*A61B 1/00* (2006.01)
*A61B 1/005* (2006.01)
(Continued)

(52) U.S. Cl.
CPC .......... *A61B 1/0057* (2013.01); *A61B 1/0005* (2013.01); *A61B 1/00009* (2013.01);
(Continued)

(58) Field of Classification Search
CPC . A61B 1/0057; A61B 1/0016; A61B 1/00172; A61B 1/00071; A61B 1/00128; A61B 1/00133; A61B 1/0051
(Continued)

(56) References Cited

U.S. PATENT DOCUMENTS 4,210,133 A * 7/1980 Castaneda .............. A61B 1/303
600/102
6,221,007 B1 * 4/2001 Green ................ A61B 1/00052
600/104

(Continued)

*Primary Examiner* — Timothy J Neal
*Assistant Examiner* — Jae Woo
(74) *Attorney, Agent, or Firm* — Richard C. Litman

(57) ABSTRACT

The image-based feedback endoscopy system includes a steering apparatus having a base platform, a pair of servomotors, a rigid tube, and a biasing member. A flexion member has a tether member and a ball screw, the tether member being in communication with the biasing member. The image-based feedback endoscopy system further includes an endoscope having a tip. The endoscope is positioned through the concentric spring such that the tip extends from the biasing member. The endoscope is in communication with the flexion member such that the endoscope is selectively movable by the pair of servomotors selectively controlling the flexion member. The endoscope includes a piezo actuator, a scanning fiber, a lens assembly, and collection fibers. The image-based feedback endoscopy system also includes an image based feedback algorithm, which selectively controls the operation of the pair of servo motors.

1 Claim, 10 Drawing Sheets

(51) Int. Cl.
  *A61B 1/307* (2006.01)
  *A61B 1/01* (2006.01)
(52) U.S. Cl.
  CPC ........ *A61B 1/0016* (2013.01); *A61B 1/00172* (2013.01); *A61B 1/01* (2013.01); *A61B 1/307* (2013.01)
(58) Field of Classification Search
  USPC ........................................ 600/146, 129, 137
  See application file for complete search history.

(56) References Cited

U.S. PATENT DOCUMENTS

| | | | | |
|---|---|---|---|---|
| 6,270,453 | B1 * | 8/2001 | Sakai | A61B 1/0055 600/141 |
| 6,939,138 | B2 | 9/2005 | Chosack et al. | |
| 7,813,538 | B2 * | 10/2010 | Carroll | A61B 1/00009 382/128 |
| 8,041,459 | B2 * | 10/2011 | Sutherland | A61B 34/75 600/407 |
| 8,721,530 | B2 * | 5/2014 | Ohline | A61B 1/0053 600/132 |
| 2005/0182295 | A1 * | 8/2005 | Soper | A61B 1/0008 600/117 |
| 2006/0149129 | A1 * | 7/2006 | Watts | A61B 1/00135 600/113 |
| 2007/0149853 | A1 * | 6/2007 | Chang | G02B 7/023 600/146 |
| 2008/0159653 | A1 * | 7/2008 | Dunki-Jacobs | A61B 1/04 382/293 |
| 2008/0262300 | A1 * | 10/2008 | Ewers | A61B 1/00071 600/114 |
| 2009/0135280 | A1 * | 5/2009 | Johnston | A61B 1/0005 348/262 |
| 2009/0208143 | A1 * | 8/2009 | Yoon | A61B 1/0058 382/321 |
| 2009/0259099 | A1 * | 10/2009 | Zhou | A61B 1/00147 600/109 |
| 2011/0152616 | A1 * | 6/2011 | Deal | A61B 1/00089 600/114 |
| 2012/0300999 | A1 | 11/2012 | Bayer | |
| 2013/0123580 | A1 * | 5/2013 | Peters | A61B 1/0057 600/118 |
| 2015/0313503 | A1 * | 11/2015 | Seibel | A61B 1/00165 600/103 |
| 2015/0346115 | A1 * | 12/2015 | Seibel | G06T 7/33 348/50 |

* cited by examiner

IMAGE-BASED FEEDBACK ENDOSCOPY SYSTEM

CROSS-REFERENCE TO RELATED APPLICATION

This application claims the benefit of U.S. Provisional Patent Application Ser. No. 61/933,758, filed Jan. 30, 2014.

BACKGROUND OF THE INVENTION

1. Field of the Invention

The present invention relates to medical devices, and particularly to an image-based feedback endoscopy system for imaging the interior of an organ of the body.

2. Description of the Related Art

Due to the relatively high recurrence rate of bladder cancer, frequent cystoscopic surveillance can be required for patients following initial diagnosis. During examination, the urologist manipulates a cystoscope to thoroughly inspect the bladder wall. These procedures can constitute a significant percentage of the urologists' workload, making bladder cancer a relatively expensive cancer to treat over the patient's lifetime.

Many minimally invasive procedures can require a clinician to manually articulate an endoscope, often in conjunction with multiple surgical tools. Manual articulation can be burdensome because endoscopes must be held steady. Further, manipulation of the hand controls may produce motion of the endoscope's tip that is non-intuitive with respect to the displayed images. These challenges may be detrimental to surrounding tissue and may increase procedure times, thereby possibly imposing considerable financial costs. Computer-controlled articulation of endoscopes could provide clinicians with greater control during diagnostic and therapeutic procedures. Previous attempts have employed image-based steering to articulate an endoscope in cardiac surgery, by directing the endoscope's tip to a position selected on the monitor. These previous attempts of image-based steering generally circumvented the difficulty of manual endoscope articulation.

Robotic assistance has also been used to avoid endoscope's tip collisions with delicate anatomical structures. Previous attempts have employed collision avoidance in arthroscopic and spinal cord procedures. For example, a robotically articulated ultrasound probe was used to enable intraoperative image-based navigation during prostatectomy. Furthermore, robotic assistance has been used to stabilize the focus of endoscopic images. For example, one approach demonstrated a system that keeps the center of a lumen at the center of the monitor's image during gastroscopic procedures. In another approach, an endoscope maintained focus on an anatomical feature in spite of periodic respiratory disturbances.

Robotically assisted surgical instruments have become commercially available within the last 20 years. Examples of these instruments include the da Vinci system (Intuitive Surgical, Sunnyvale, Calif.), which has improved clinician dexterity in many FDA-approved procedures. Another example is the FDA-approved ROBODOC assists surgeons in hip and knee arthroplasty procedures (CUREXO Technology Corporation, Freemont, Calif.

A newer approach to diagnostic procedures involves fully automating surveillance in order to eliminate the need for direct clinician oversight. Procedures not requiring clinician oversight could be advantageous because they may be administered by PAs, which further reduces cost and increases patient access to care. An example of such a procedure is wireless capsule endoscopy (WCE). During WCE, a pill camera captures images of a patient's digestive tract after being swallowed. Since WCE does not require the clinician to directly oversee the procedure, a PA may administer WCE and gathered data can be digitally transmitted for expert analysis. Allowing PAs to administer surveillance may also reduce the workload of busy clinicians.

Flexible endoscopes have a forward-view (or limited a few angles available) with a limited field-of-view age size. The performance and sensitivity of the manually-operated endoscopy surveillance depends on the care, memory, ability and experience of the operating clinician, since it only allows an operator to see a quite small portion of the surface of the organ. These challenges may increase procedure times, there by imposing considerable financial costs, and decrease sensitivity of the procedure.

Thus, an image-based feedback endoscopy system solving the aforementioned problems is desired.

SUMMARY OF THE INVENTION

The image-based feedback endoscopy system includes a steering apparatus having a base platform, a pair of servomotors, a rigid tube, and a biasing member. Additionally, a flexion member has a tether member and a ball screw, the tether member being in communication with the biasing member. The image-based feedback endoscopy system further includes an endoscope having a tip. The endoscope is positioned through the concentric spring such that the tip extends from the biasing member. The endoscope is in communication with the flexion member such that the endoscope is selectively movable by the pair of servomotors selectively controlling the flexion member. The endoscope includes a piezo actuator, a scanning fiber, a lens assembly, and collection fibers. The image-based feedback endoscopy system also includes an image-based feedback algorithm, which selectively controls the operation of the pair of servo motors.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The image-based feedback endoscopy system validates that a target organ is comprehensively imaged, so that a 3-D mosaic of the captured images from the video can be created in real time. This mosaic is constructed from the endoscopic image frames that are stitched into a single seamless composite. The benefit of this mosaic is that it provides a global perspective of the entire internal surface in a single stitched image that can be quickly reviewed, and serves as validation that overlapping images are well aligned and that there are no missing regions.

Figure 1:
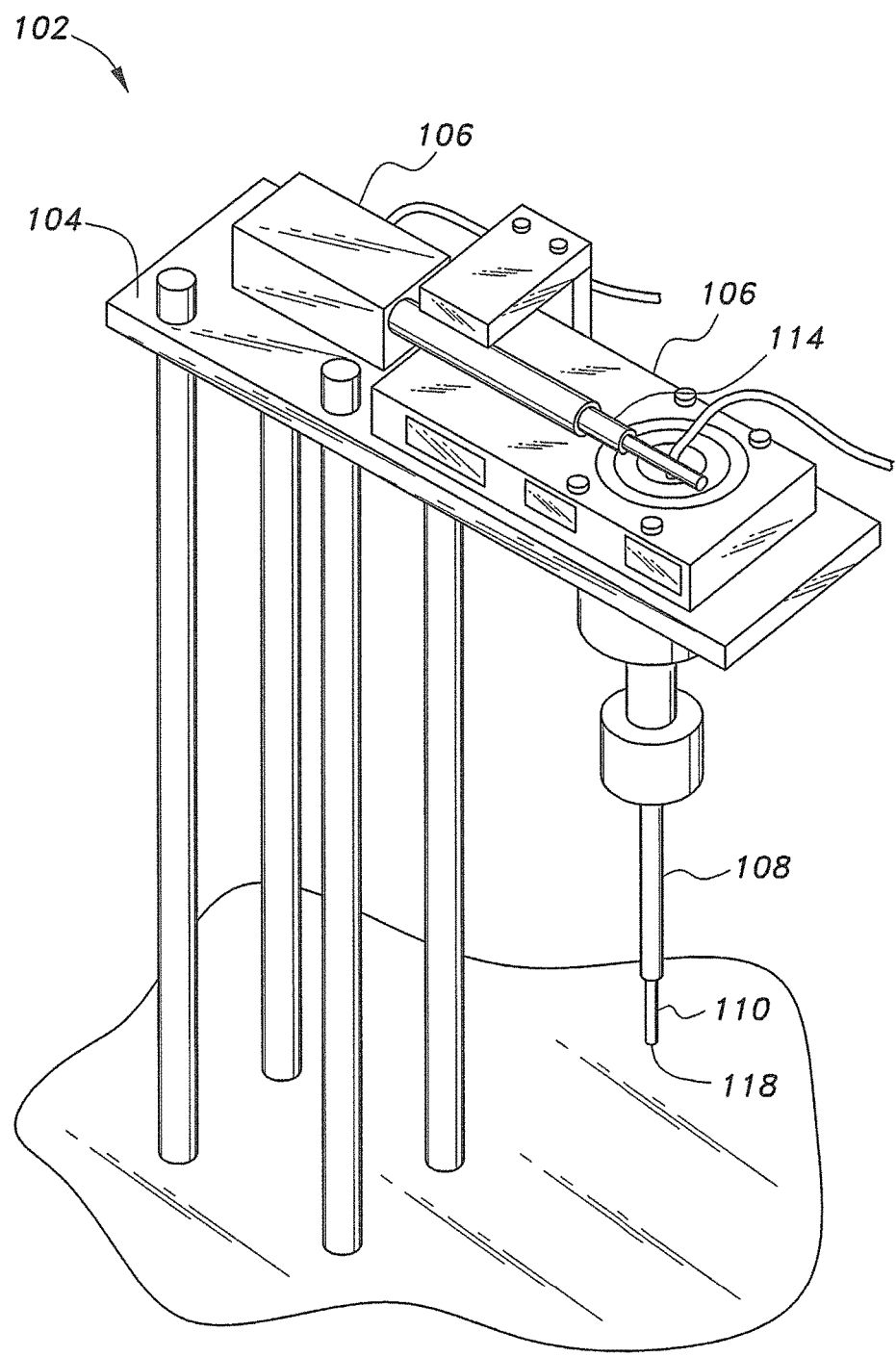
FIG. 1 is a perspective view of a steering apparatus of an image-based feedback endoscopy system according to the present invention.

As shown in FIG. 1, the image based feedback endoscopy system 100 includes a steering apparatus 102. The steering apparatus 102 can be used on a bench top and includes a base platform 104, two servomotors 106, a rigid brass tube 108, and a concentric spring 110.

Figure 2:
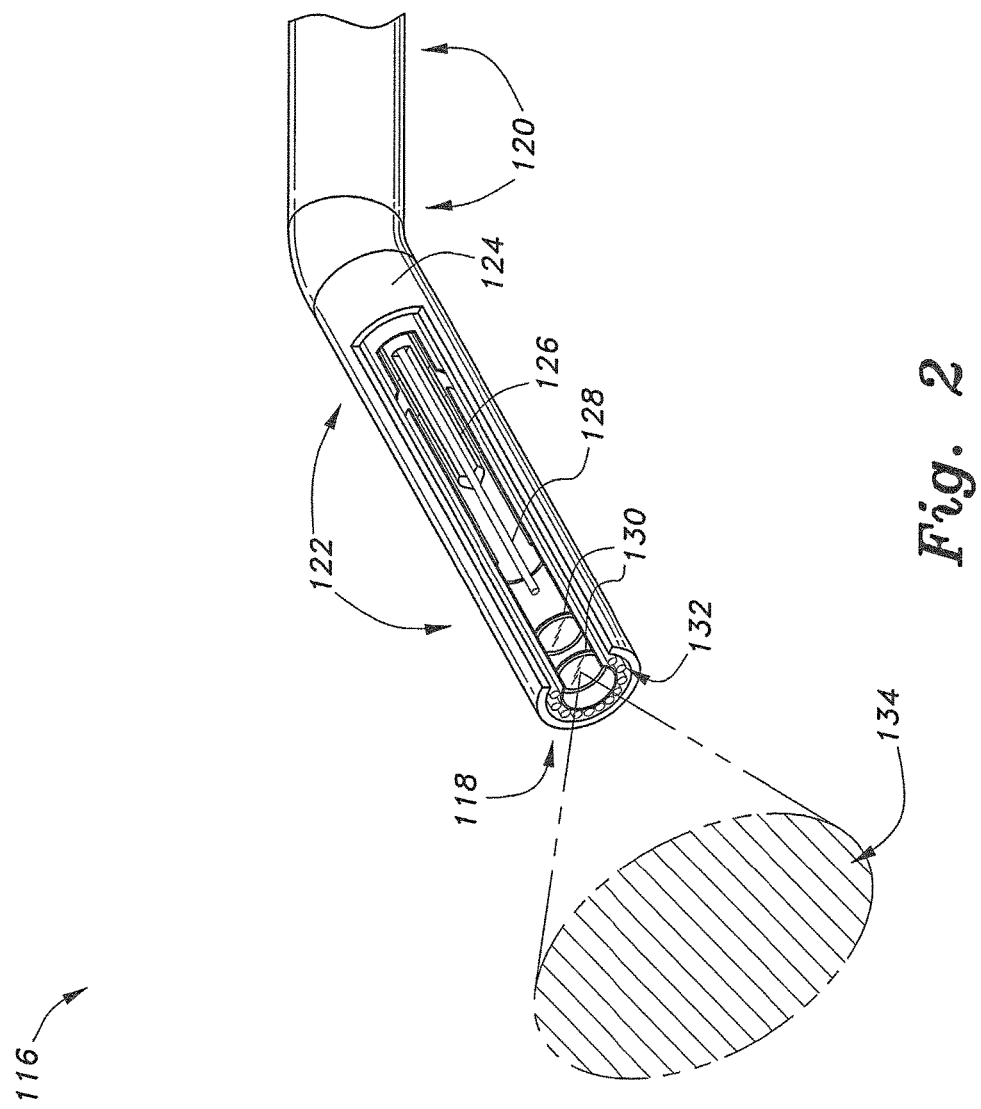
FIG. 2 is a partial perspective view of an endoscope in an image-based feedback endoscopy system according to the present invention, shown broken away to show details of the structure in the interior of the endoscope.

In addition to the steering apparatus 102, an endoscope 116 (shown in FIG. 2) is included with the image based feedback endoscopy system 100. The endoscope 116 is a miniature laser-scanning fiber endoscope (SFE). Unlike conventional endoscopes that possess a large outer diameter (>5 mm), the SFE produces 600×600 line images within a 1.2 mm housing. This dramatic reduction in size could allow cystoscopy to be performed with greater ease of insertion and reduced patient discomfort, possibly without anesthesia. The SFE endoscope 116 also has an extended depth of focus of 50 mm, which helps maintain focus in the bladder during procedures. These properties of the SFE endoscope 116 make it ideal for automating cystoscopic examination. It should also be noted that other miniature flexible endoscopes might be compatible with our automated steering apparatus.

The SFE endoscope 116 captures wide field-of-view (FOV), high-resolution images at video frame rates. Images are scanned by delivering red, green, and blue laser light through a single-mode optical fiber driven at mechanical resonance by a piezoelectric actuator 126 at the distal tip 118 of the endoscope 116. As laser light is scanned over a surface, back-scattered light is collected at the proximal end of the scope 116 through a concentric ring of collection fibers 132 that surround a lens assembly 130. With its largest diameter measuring 1.2 mm, the SFE 116 allows visualization of previously inaccessible anatomies.

Figure 3:
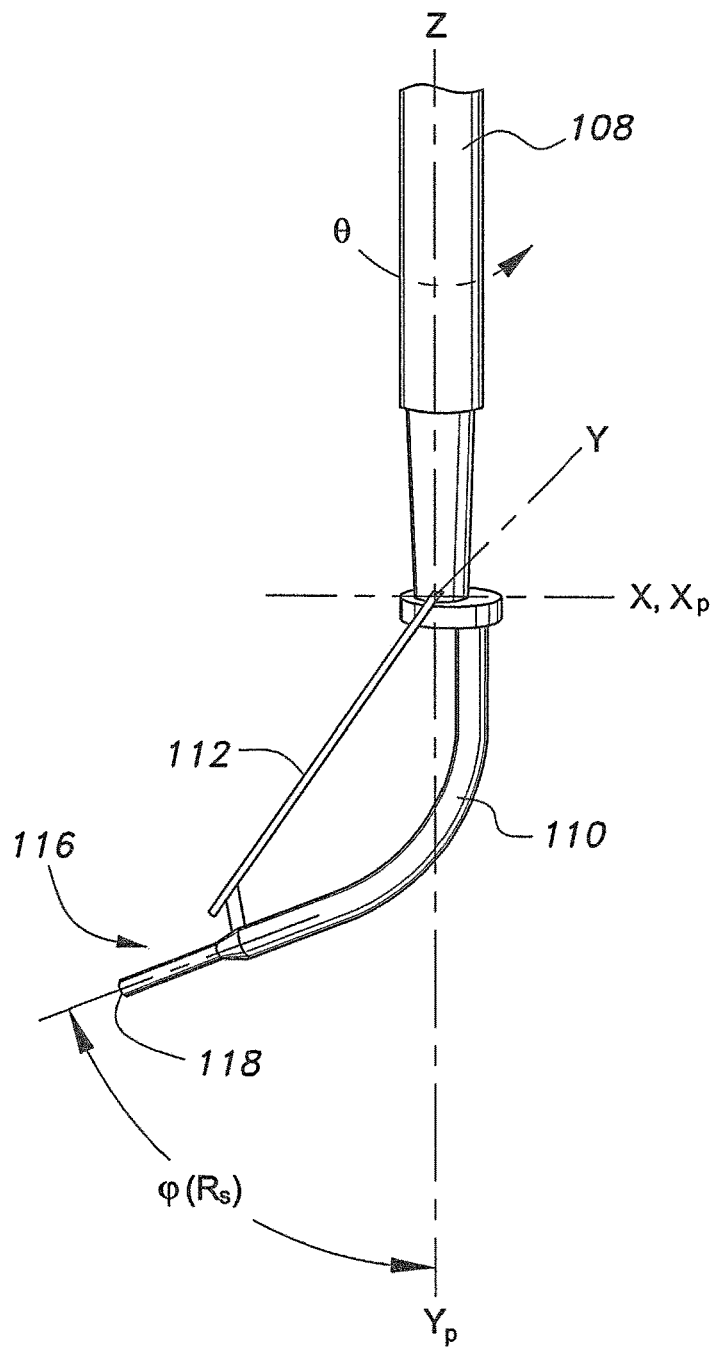
FIG. 3 is a partial front view of an endoscope and rigid tube of an image-based feedback endoscopy system according to the present invention.

The servomotors 106 in the steering apparatus 102 control flexion of the SFE endoscope tip 118 and rotation of the rigid brass tube 108. Flexion is controlled by a Kevlar tether 112 (shown in FIG. 3) wound around a Newport CMA-25CCCL ball screw 114. The tether 112 runs the length of the rigid tube 108 and attaches to the distal end of a concentric spring or biasing member 110 connected to the rigid tube 108, as shown in FIG. 3. As the ball screw 114 is wound, tension in the tether 112 causes the SFE endoscope tip 118 to bend. The spring 110 overcomes the slight pre-curve in the SFE endoscope 116 and ensures that the SFE endoscope 116 consistently returns to the same position when the tether 112 is fully relaxed. A Newport PR50PP rotational servomotor 106 controls rotation of the rigid tube 108. SFE articulation is controlled by a LabView program (National Instruments, Austin, Tex.) that sends commands to an ESP 300 motion controller through a USB interface and on to the servomotors. Simulated scans were conducted in a 4.5-in diameter spherical light bulb bladder phantom, as described below.

Each steering servo outputs a measurement of its absolute motion that is initially unrelated to the position and orientation of the SFE. The ball screw 114 outputs Rs, in mm, which is proportional to the length of tether 112 reeled in or out. The rotational servo outputs a measurement θ of the rotation of the rigid shaft. To adequately control SFE articulation, an initial image-based calibration is performed to characterize the relationship between the servomotor 106 outputs, Rs and θ, and endoscope articulation expressed as 3-D position (x, y, z) and pose (θ, φ), shown in FIG. 3. Calibration is required only once to characterize the system's mechanical components and does not need to be performed again unless the configuration is changed.

Motion of the SFE's distal tip 118 is tracked using a calibrated webcam (Logitech, Freemont, Calif.) placed orthogonal to the XY plane, defined by θ=0°, in front of a white background. One hundred successive images are captured for incremental changes in $R_s$ through a bend angle of near φ=180°. For each image, the position and orientation of the SFE's tip 118 is computed using Canny edge-detection as part of MATLAB's image processing toolbox. After extracting prominent edges, candidate edges are identified for each image on the basis of pixel length and straightness corresponding to the SFE tip 118. The edge component with the greatest distance is selected as the SFE tip 118 and defined by a pixel position $(X_P, Y_P)$ relative to the brass insertion tube, and orientation φ determined by the slope of the detected edge. The end result is 100 data points expressing the SFE tip's pixel position and tip-bending angle as functions of $R_s$ as the tip bends to φ=180°. Polynomials $P_{xp}$, $P_{yp}$, and $P_φ$, are fit to the data as a function of the spool measurement $R_s$. Finally, the servomotor 106 outputs are converted into 5 DOF position and orientation by (1)-(4), where α is a scalar used to convert from pixel space to metric space in mm/pixel and θ is in radians.

The relationship is described below in the following equations:

$$x = P_{xp}(R_s) * \cos(θ) * α \quad (1)$$

$$y = P_{xp}(R_s) * \sin(θ) * α \quad (2)$$

$$z = -P_{yp}(R_s) * α \quad (3)$$

$$φ = P_φ(R_s). \quad (4)$$

To determine the reliability of the steering apparatus 102, comparing multiple images acquired at randomly selected coordinates within a bladder phantom performed a positional repeatability study. The SFE endoscope 116 was sequentially navigated through ten unique locations, acquiring an image at each point. Following navigation to each of the ten coordinates, the SFE endoscope 116 was relaxed back to its initial position and subsequently re-navigated back through each location a total of four times without reinserting. Repeatability in SFE articulation was assessed by measuring shift between corresponding images at each location.

Quantitatively, image shift was determined by calculating image overlap using a feature-based image alignment method. By comparing the latter three images of a set to the baseline image acquired at each location, an average overlap percentage of 97.75% was computed. Assuming that the contribution of image noise to overlap error is negligible, mechanical drift contributed roughly 1.75% overlap error as a worst case scenario. Creep in the Kevlar spool, SFE tip 118 movement, or hysteresis in the system may cause this slight positional error. Given the SFE's FOV and distance to the bladder surface, omnidirectional mechanical drift is estimated as 2 degree rotational error or 1 mm positional error on the bladder's surface. The 1 mm error in positioning the SFE full cone-viewing field of 49 mm diameter on the phantom surface is less than 3%. This error was due to mechanical drift and was deemed tolerable.

Figure 4B:
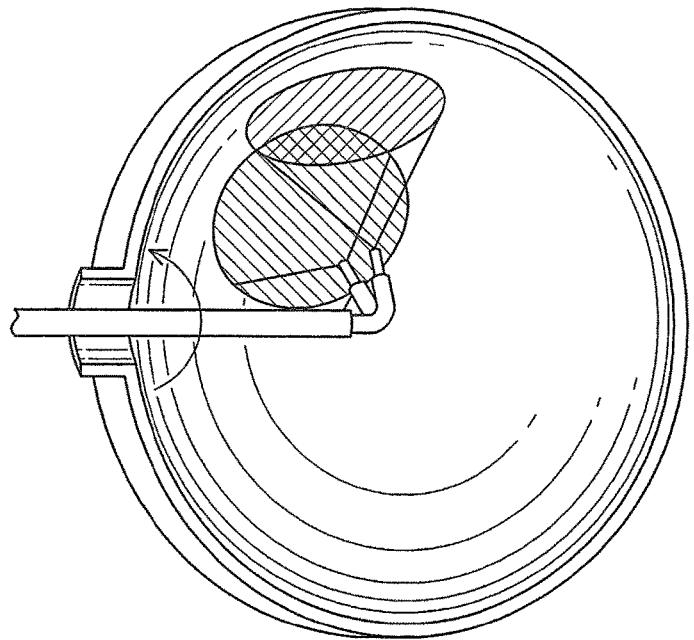
FIG. 4B is a schematic diagram showing latitudinal overlap in the trajectory of successive images in an image-based feedback endoscopy system according to the present invention.
Figure 4A:
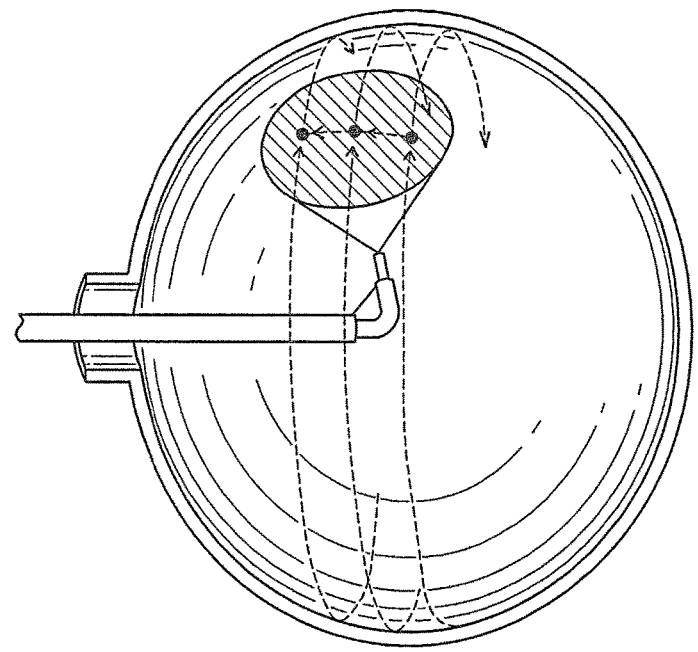
FIG. 4A is a schematic diagram showing the trajectory of latitude sweeps and spacing of longitudinal steps in an image-based feedback endoscopy system according to the present invention.
Figure 4C:
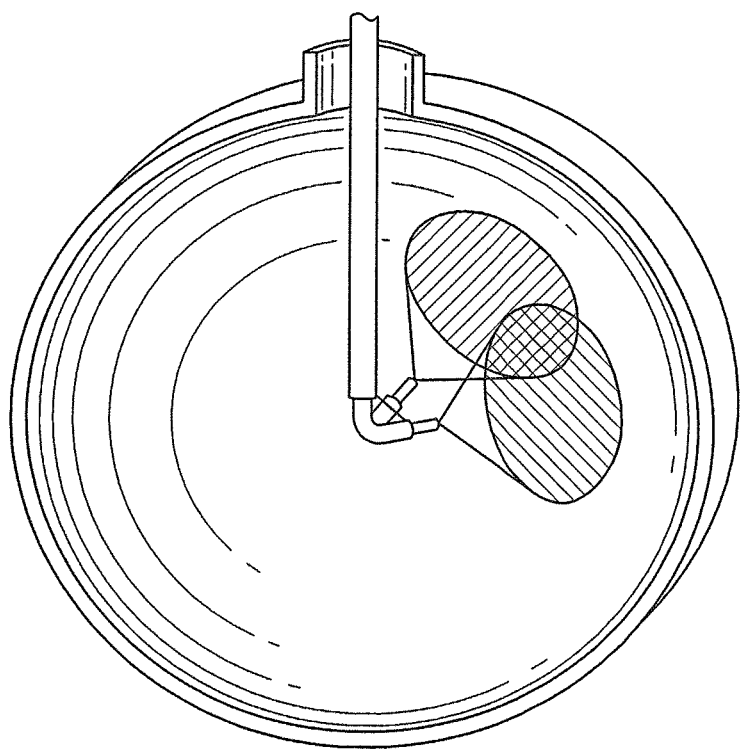
FIG. 4C is a schematic diagram showing longitudinal overlap in the trajectory of successive images in an image-based feedback endoscopy system according to the present invention.

Using the mathematical model of the endoscope's position and orientation as a function of the servomotor's outputs, a spherical scan trajectory was devised for comprehensive imaging of a bladder phantom's surface, as shown in FIG. 4A. This spherical scan is composed of latitudinal sweeps (rotating θ through 360 degrees) separated by small longitudinal steps. Each longitudinal step occurs by incrementally bending the endoscope's tip by an angle $\Delta\varphi$. Latitudinal sweeps occur until the endoscope's tip bending angle reaches 180 degrees. Because the geometry of the bladder and the endoscope's position in relation to the bladder are unknown, the scan trajectory is adaptively computed using image-based feedback. Specifically, incremental motion changes of $\Delta\theta$ and $\Delta\varphi$ are optimized by comparing overlap between each pair of successive images during a latitudinal sweep, shown in FIG. 4B, and between overlapping images following a longitudinal step, shown in FIG. 4C. By verifying that each image overlaps with adjacent images, we ensure comprehensive surveillance and an efficient scanning trajectory that minimizes image redundancy and procedure time as well as yields a succinct set of representative images for review by the urologist.

For any pair of adjacent images separated by a small positional change $\Delta\theta$ or $\Delta\varphi$, a fractional overlap percentage ω is computed on the basis of some shared set of features computed using a scale-invariant feature transform (SIFT). These SIFT features are quantified by descriptors that are insensitive to rotation and scale, allowing them to be matched between images regardless of small changes in their location and orientation. From a subset of shared features, it is possible to compute a homography or perspective transformation that aligns a pair of images. From two frames matched by a set of corresponding features, an underlying homography is computed that defines the transformation between pixels in both images. The overlap ω is then measured as the average fractional area in pixels that maps within the active image area of both frames.

Figure 6:
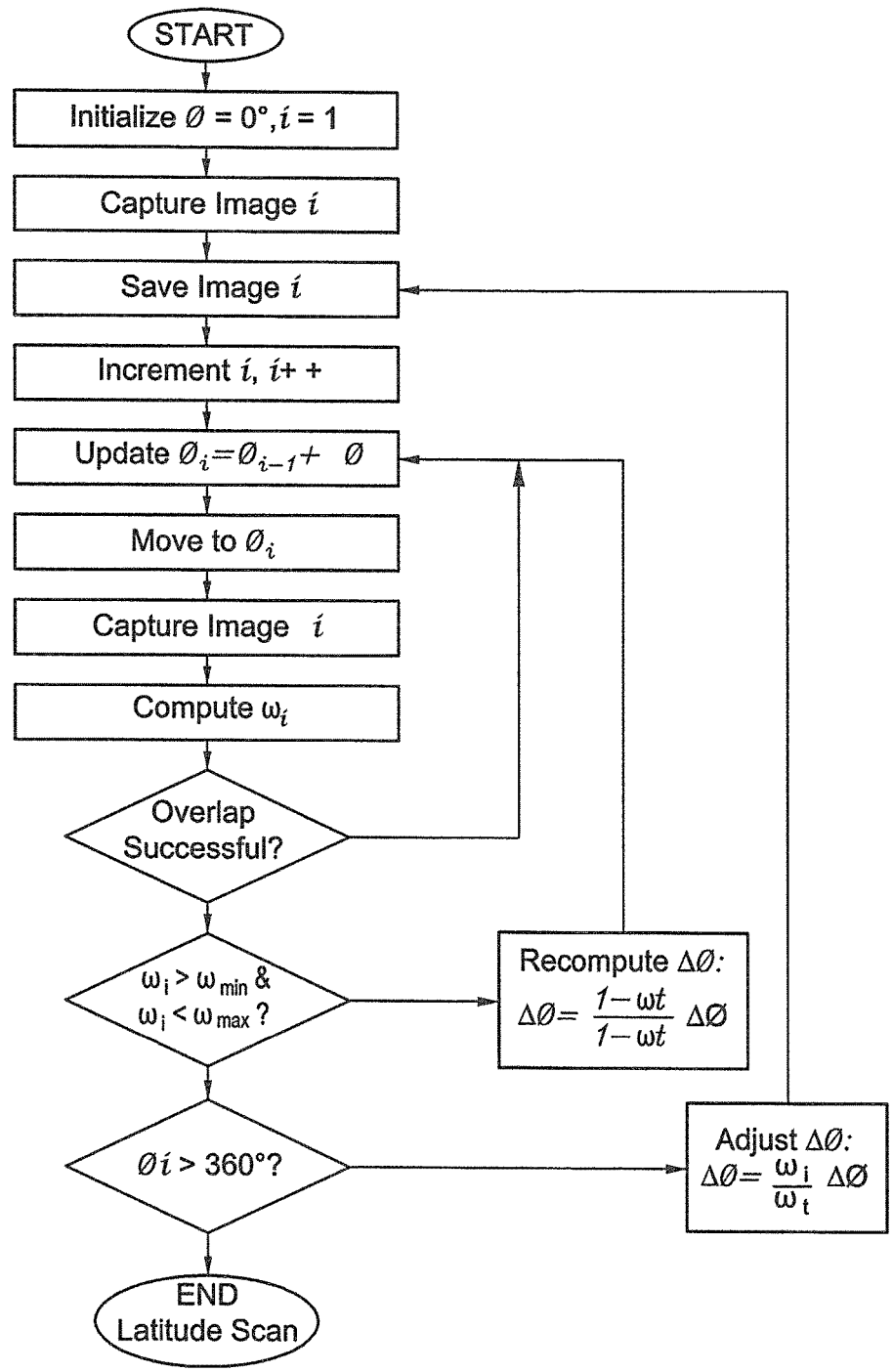
FIG. 6 is a flowchart of an algorithm used in an image-based feedback endoscopy system according to the present invention.

Each scan is initialized with the endoscope pointed nearly straight with only a slight bend angle. A latitudinal scan is then conducted following the steps shown in FIG. 6. Each latitudinal scan begins at θ=0 degrees and scans through 360 degree rotation. At the beginning of each scan an initial image is captured and saved. Following each saved image, the endoscope is rotated by an initial $\Delta\theta$ to a new position to acquire the next image. The overlap ω is computed between the successive images. If no overlap is computed due to an insufficient number of matched features, $\Delta\theta$ is halved and the image is reacquired. If ω is successfully computed we determine whether it is within an acceptable range, $\omega_{min}$ to $\omega_{max}$. If it is not, we compute a new estimate of the rotation step $\Delta\theta$:

$$\Delta\theta_{new} = \frac{1-\omega_t}{1-\omega_t}\Delta\theta. \tag{5}$$

The value of $\Delta\theta_{new}$ computed from (5) is updated assuming that there is some target overlap amount ωt and that ω decreases approximately linearly for small $\Delta\theta$. The minimum overlap $\omega_{min}$ is set to 0.6 to ensure enough shared features are identified from which to confidently assert that two images indeed overlap. The upper limit $\omega_{max}$ is set to 0.9 to prevent unnecessary image redundancy and excessive data collection. The target overlap ωt is set to 0.7. Once ω is within the acceptable range, the image is saved and the endoscope is once again moved to a new position to capture the next image. For each saved image, the initial $\Delta\theta$ is slightly adjusted to a value $\Delta\theta_{new}=(\omega_t/\omega_t)\Delta\theta$, to achieve the target overlap $\omega_t$.

Figure 5B:
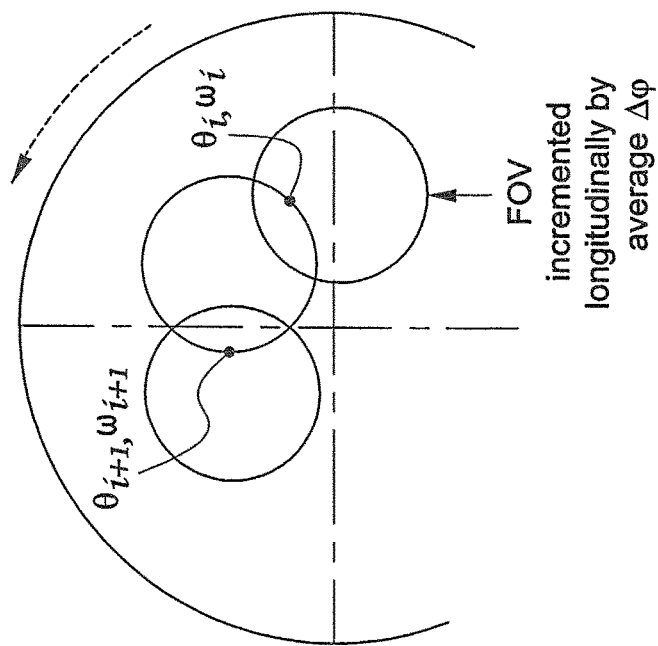
FIG. 5B is a schematic diagram showing trajectory once the endoscope returns to θ=0 degrees in an image-based feedback endoscopy system according to the present invention.
Figure 5A:
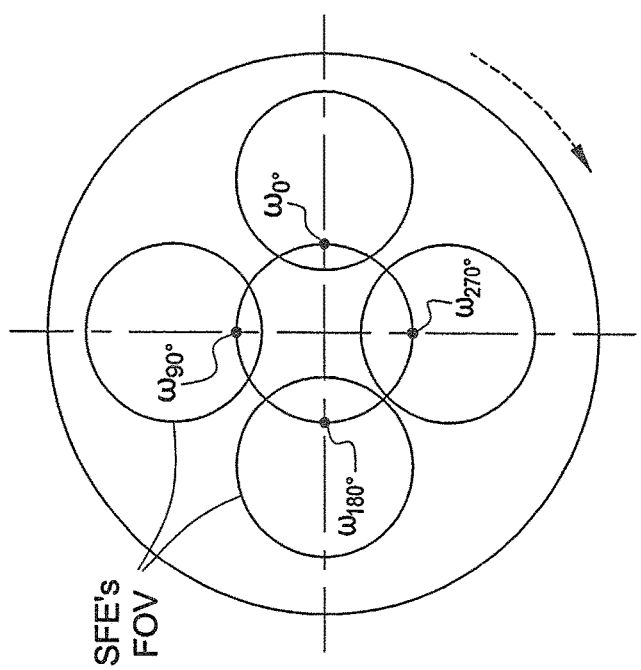
FIG. 5A is a schematic diagram showing trajectory adjustment by rotating θ clockwise so that longitudinal overlap optimizations are conducted between the FOV of successive images by adjusting φ along four cardinal directions in an image-based feedback endoscopy system according to the present invention.

Following each latitudinal sweep in θ, a small longitudinal step $\Delta\varphi$ is taken before performing a subsequent latitudinal sweep. This small step is made by retracting the tether by a small amount, thereby bending the endoscope back slightly. In this way, each latitudinal sweep provides a new layer of image data that overlaps with the previous sweep. To ensure successive sweeps adequately overlap, $\Delta\varphi$ is optimized along four cardinal longitudes, defined at θ=0°, 90°, 180°, and 270°, as shown in FIG. 5A. The endoscope rotates θ clockwise to obtain each of the four longitudinal overlap optimizations. Each optimization is performed in the same way as for each latitudinal step $\Delta\theta$ described previously. Once the system has completed the four longitudinal optimizations and θ=0°, $\Delta\varphi$ is computed from the average of the optimized values of $\Delta\varphi_0$, $\Delta\varphi_{90}$, $\Delta\varphi_{180}$, and $\Delta\varphi_{270}$. After φ has been incremented, another latitudinal sweep is conducted in the counterclockwise direction, as shown in FIG. 5B. Rotation of θ alternates between clockwise and counterclockwise to avoid excessive twisting of the SFE.

Four automated scans were conducted in the bladder phantom using the algorithm described in the previous section. The bladder phantom was filled with water during the scans to minimize specular reflection in the images and to more closely simulate scans in a saline-filled bladder. Each scan used an SFE with an 88° FOV that produced 600×600 line images. In the first trial, the steering apparatus was placed at the spherical center of the phantom. The minimum distance between the SFE and the inner area was approximately 25.4 mm. During the first scan, the apparatus traversed 13 latitudes with an average increment between latitudinal images $\Delta\bar{\theta}$ of 9.58°. A total of 508 images were captured during the first trial. Second, the apparatus was kept at the same depth as the first trial, but displaced approximately 12.5 mm along the x-axis. The minimum distance between the SFE and the phantom surface was approximately 13 mm. Displacing the apparatus laterally simulates a more realistic cystoscopy, where the cystoscope may be askew to one side of the bladder. The second scan captured the inner surface area in 726 images, with a smaller $\Delta \bar{\theta}$ of 6.85°. The steering apparatus traversed 14 latitudes in the second trial, where the last latitude contained images of the insertion hole.

In the third trial, the apparatus's xy position corresponded with the phantom's spherical center but the apparatus was displaced along z approximately 25.4 mm. Displacing the apparatus along z simulates a cystoscopy where the cystoscope was not pushed to the optimal imaging depth. This scan captured the inner surface in 13 latitudes, 656 captured images, and an average latitudinal increment of 7.38°. The acceptable overlap percentage range for adjacent images in the previous three trials was between 60% and 90%. To assess the effect of decreasing the overlap percentage range, the fourth trial altered the acceptable overlap range to [50%, 80%] conducted near the phantom's spherical center. The target overlap for the fourth trial was set to 60%. The phantom's inner surface was captured by 445 images with a noticeably larger average latitudinal increment of 12.84 degrees. During the fourth trial, the apparatus traversed 15 latitudes, where the last latitude imaged outside of the phantom.

Figure 7A:
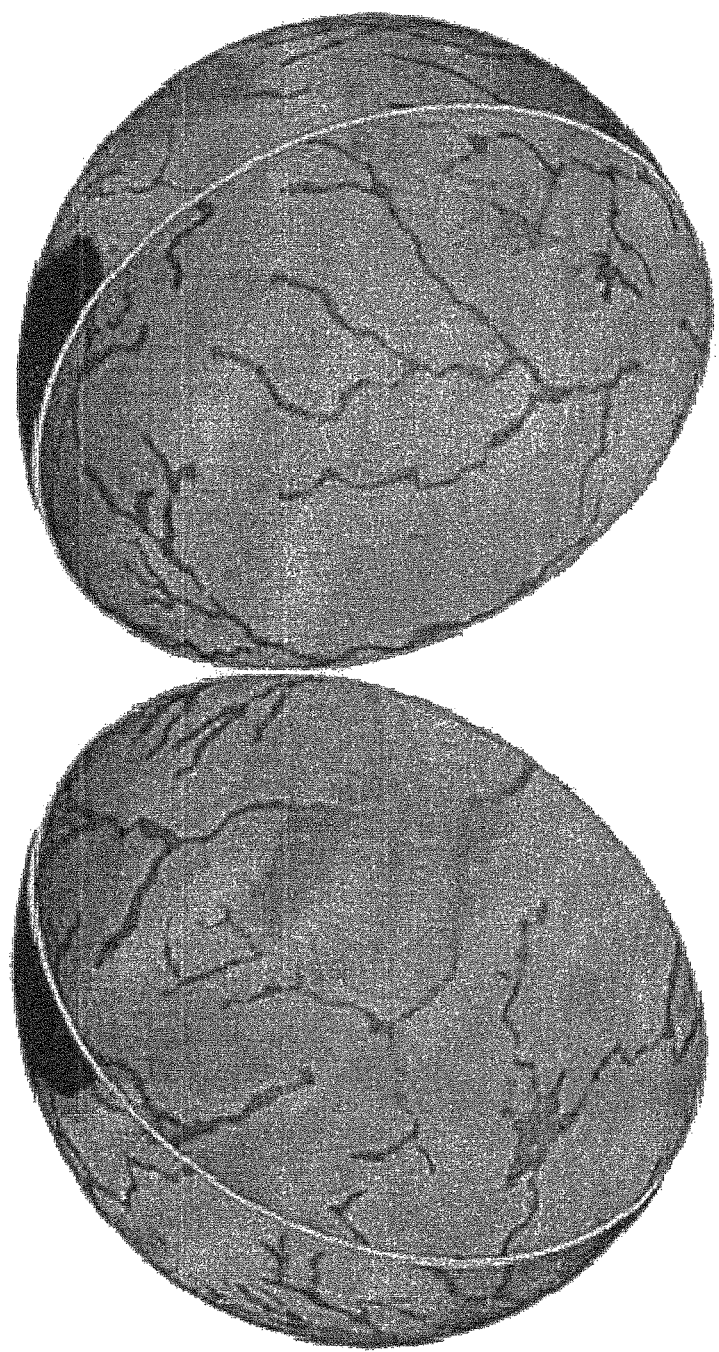
FIG. 7A is a hinged view of the 3-D mosaic of a bladder phantom generated from captured images during the first automated scan in an image-based feedback endoscopy system according to the present invention.

To validate that the bladder phantom was comprehensively imaged, a 3-D mosaic of the captured images from the first trial was created, as shown in FIG. 7A. This mosaic is constructed from post-processing of the endoscopic image frames that are stitched into a single seamless composite. The entire stitching process currently requires roughly 30 minutes to complete using a Dell 470 Precision Workstation (3.40 GHz). The benefit of this mosaic is that it provides a global perspective of the entire internal surface in a single stitched image that can be quickly reviewed, and serves as validation that overlapping images are well aligned and that there are no missing regions.

Figure 7B:
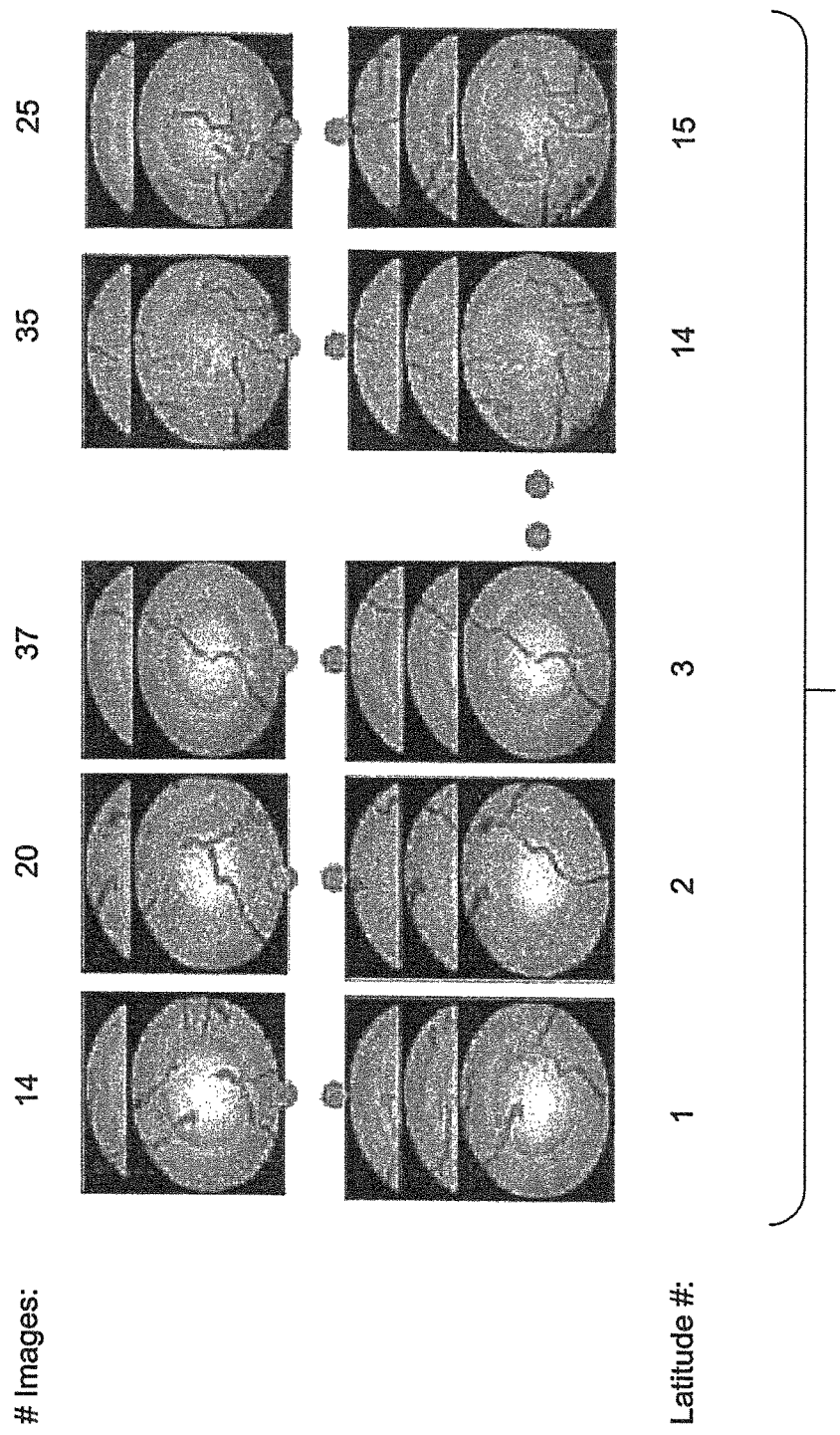
FIG. 7B is successive list of representative images of the bladder phantom, organized by latitude, in an image-based feedback endoscopy system according to the present invention.
Figure 8:
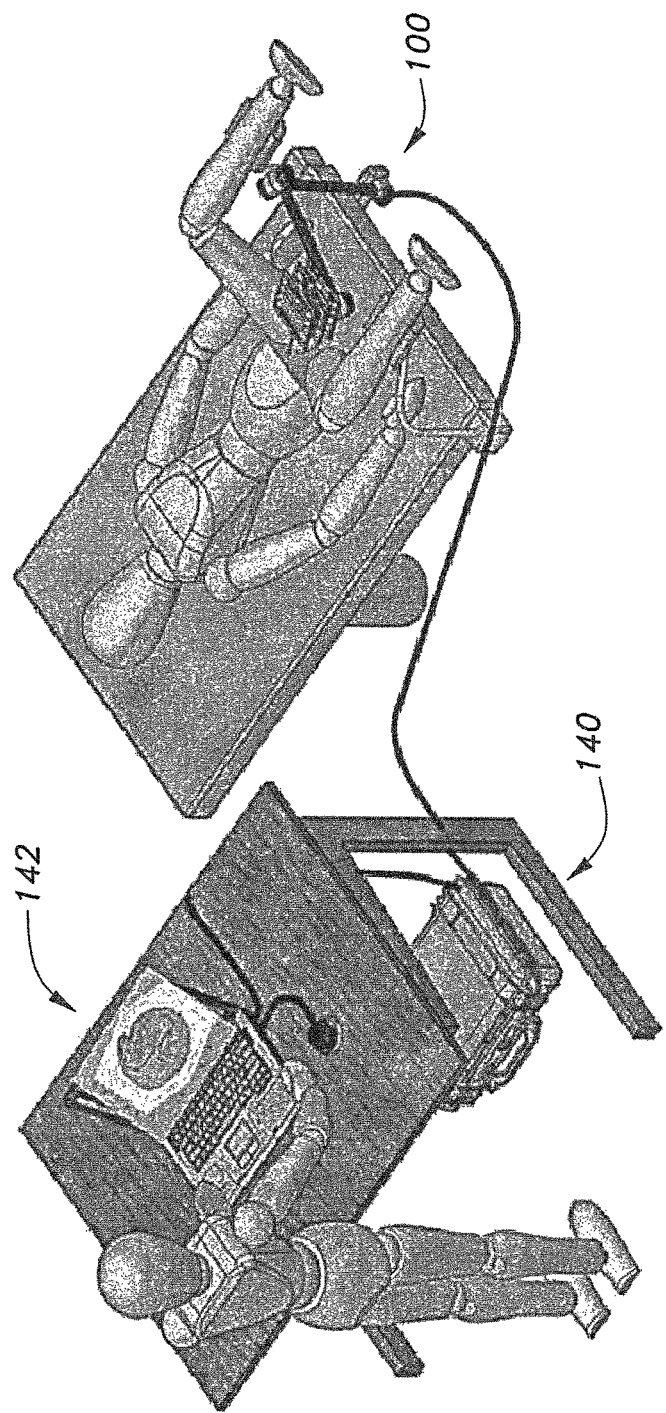
FIG. 8 is a schematic diagram showing use of an image-based feedback endoscopy system according to the present invention.

Although a number of applications have pursued cystoscopic image stitching over localized regions of the bladder, this approach is unique in that it focuses on full 3-D reconstruction using structure from motion software and is ideally suited to an automated approach to bladder surveillance. Only a small hole is present in the mosaic, corresponding to the uncovered top portion of the phantom. The entrance hole of the phantom is shown at the top of FIG. 7A as a black circle. The overall accuracy of the stitched image is evaluated on the basis of the pixel projection error, which is the measure of misalignment between all matched features. For this mosaic, the root-mean-squared projection error was 3.87 pixels. From FIG. 7A, all portions of the bladder are visible, except where the apparatus entered the phantom, at which point the scan was stopped. No other voids are present in the mosaic. In practice, a mosaic could be created and digitally transmitted to the clinician for diagnosis. Or, a succession of representative images could be reviewed, similar to WCE and conventional cystoscopy, as shown in FIG. 7B.

The previous trials confirm that a robotically articulated endoscope that uses adjacent image overlap as trajectory feedback can provide comprehensive coverage of a bladder phantom. Whereas robotic assistance has previously been used to augment clinician control, the outlined approach eliminates the clinician from the procedure entirely. A subset of images or video acquired from the procedure can then be stored or transmitted for expert review. However, clinical validation has not been demonstrated, as no diagnosis from bladder images has been attempted.

The results indicate that automated surveillance was successful, even when the apparatus was displaced from the bladder phantom's spherical center. However, this required longer scan durations and an increase in the number of acquired images. More images were captured as the apparatus was placed off-center as a result of asymmetrical changes to the FOV image size. For example, when the apparatus is placed above the phantom's spherical center, one hemisphere is closer to the SFE's tip than the other. As a result, the FOV image size is smaller for the hemisphere closer to the SFE and requires more images to capture. This occurs when the SFE is laterally displaced from the phantom's spherical center as well.

Incorporating insertion-depth control into the steering apparatus may circumvent a limited FOV image size. Currently, the apparatus is mechanically restrained to a constant insertion depth for simplicity. However, control over insertion depth is often needed to obtain an optimal distance between commercial cystoscopes and a patient's bladder. A future device may feature manual or automatic insertion depth control to help find an optimal imaging distance and reduce the number of captured images.

Our findings also suggest that lowering the acceptable overlap percentage range may reduce the number of representative images. If a patient's bladder can be comprehensively imaged in fewer images, the procedure would theoretically be faster to perform due to fewer endoscopic sweeps. When the acceptable overlap percentage range was lowered by 10%, the number of representative images decreased by 63 and $\Delta \theta$ increased by 3.26° when compared to the same scan with a 10% higher overlap range. Image redundancies are reduced when lower overlap ranges are used because images with high overlap percentages trigger the servomotors to increase the increment separating the images. However, the probability of a missed match between overlapping image regions increases with step size. For instance, there was an 82% increase in failed adjacent image overlaps when the target overlap was set to 60%, as opposed to 70%. To minimize the number of missed overlapping image pairs, the more conservative overlap target value of 70% was used.

The presence of features within the bladder phantom impacted the system's performance in the trials. The apparatus struggled to overlap neighboring images in portions of the bladder with few features. Conversely, the system quickly overlapped neighboring images when features were abundant in the captured frames. The dependence of system performance on bladder features necessitates evaluating the automated system's performance in an actual bladder. The mosaicking algorithm has already been validated in an excised pig bladder. Our next step will be to determine if automated trajectory control can be used in conjunction with mosaicking to comprehensively scan the pig's bladder.

Changes to programming architecture and a different selection of servomotors will decrease the duration of automated surveillance. Currently, automated scans complete within approximately 2 hours. Although the objectives for the proof-of concept steering apparatus were not concerned with the time efficiency of the scan, future work must focus on reducing overall procedure time for clinical relevance.

The long duration is primarily the result of a slow interface between LabView and the image analysis software compiled as a MATLAB executable. From our experiments, each overlap measure took approximately 1 second to perform. Integrating the image analysis and servo control software, as well as utilizing accelerated hardware, such as a GPU, will greatly diminish overall procedure time. Presuming the image analysis software can be run in real time with acquired video, the procedure duration is estimated to be around 20 minutes with the current motors, which is the time required to scan the bladder phantom without stopping.

Additional gains in expediency can be realized by faster scanning of the endoscope. The Newport PR50PP and CMA-25CCCL are intended for applications requiring sub-degree and sub-millimeter precision, respectively. The dynamics of the system are largely defined by the PR50PP motor, which has 0.01° angular precision and a maximum velocity of 20°. Since this level of precision contributes to a negligible positioning error at the expense of a slow maximum speed, a servomotor with moderate speed and precision may be substituted to decrease system latency. The desired outcome is to conduct image overlap analysis in real time such that the automated scan duration is comparable to manual cystoscopies, or around 10 minutes.

Although the steering apparatus scanned a spherical bladder phantom, the approach may be used within a patient's bladder as well. Our apparatus bent the SFE with a minimum bend radius of 7 mm and a maximum lateral (xy) displacement of 31.75 mm from the rigid tube. A patient's distended bladder, although nonspherical, is mostly concave and typically larger than the apparatus's range of motion. Thus, it is expected that our approach could be used to inspect a patient's bladder if the SFE could be navigated near the center of the bladder. Further work is needed to transition the experimental setup into a handheld or easily portable device. Collision detection and avoidance could be implemented in order to improve patient safety. Monitoring the bending and axial forces that act on the endoscope's tip may also be a simple way to avoid tip collisions in a handheld device. Smaller motors could be situated away from the distal tip, similar to the Kevlar tether method used in this experiment. Distancing the servomotors and control electronics from the portion of the cystoscope that enters patients could help facilitate FDA approval of a handheld, automatic device.

It is to be understood that the present invention is not limited to the embodiments described above, but encompasses any and all embodiments within the scope of the following claims.

We claim:

1. An image-based feedback endoscopy system for robotically controlling the movements of an endoscope, comprising:
   a steering apparatus having:
      a base platform;
      a pair of rotational servomotors mounted on the platform;
      a ball screw operatively connected to the pair of rotational servomotors;
      a rigid tube operatively connected to the servomotors for rotational movement;
      a concentric spring having opposed ends, wherein one end is operatively connected to the rigid tube; and
      a tether operatively connected at one end to the ball screw and extending through the rigid tube and the concentric spring and extending outwardly from the distal end of the concentric spring and being attached to the distal end of the concentric spring;
   a laser-scanning fiber endoscope, the endoscope having a tip, the endoscope being positioned through the concentric spring such that the tip extends therefrom, the endoscope being in operative communication with the tether such that the endoscope is directly movable by the pair of servomotors selectively controlling the tether; and
   an image-based feedback algorithm, the image-based feedback algorithm selectively controlling operation of the pair of servomotors based on the ball screw movements which is proportional to the length of the tether reeled in or out.

* * * * *